US00PP18723P3

(12) United States Plant Patent
Giesen

(10) Patent No.: US PP18,723 P3
(45) Date of Patent: Apr. 8, 2008

(54) ***ARGYRANTHEMUM* PLANT NAMED 'ARG WHIT'**

(50) Latin Name: *Argyranthemum frutescens*
Varietal Denomination: Arg Whit

(75) Inventor: Eric Giesen, Andijk (NL)

(73) Assignee: Goldsmith Seeds Inc., Gilroy, CA (US)

( * ) Notice: Subject to any disclaimer, the term of this patent is extended or adjusted under 35 U.S.C. 154(b) by 312 days.

(21) Appl. No.: 11/206,284

(22) Filed: Aug. 18, 2005

(65) Prior Publication Data

US 2007/0044191 P1 Feb. 22, 2007

(51) Int. Cl.
*A01H 5/00* (2006.01)

(52) U.S. Cl. ..... Plt./263

(58) Field of Classification Search ..... Plt./263
See application file for complete search history.

*Primary Examiner*—Wendy C. Haas
*Assistant Examiner*—Georgia Helmer
(74) *Attorney, Agent, or Firm*—Jondle & Associates, P.C.

(57) ABSTRACT

A new *Argyranthemum* plant particularly distinguished by its compact, rounded, growth habit, excellent branching, very early flowering, good heat tolerance, and large white flowers is disclosed.

1 Drawing Sheet

Genus and species: *Argyranthemum frutescens.*
Variety denomination: 'Arg Whit'.

BACKGROUND OF THE NEW PLANT

The present invention comprises a new and distinct cultivar of *Argyranthemum,* botanically known as *Argyranthemum frutescens,* and hereinafter referred to by the cultivar name 'Arg Whit'. The new cultivar originated from a hybridization made in 2002 in Andijk, The Netherlands. The female parent is *Argyranthemum* 'ARO-2-6-1' an unpatented white *Argyranthemum* proprietary line, and the male parent is *Argyranthemum* 'ARO-2-15-1' an unpatented white *Argyranthemum* proprietary line.

The new cultivar was created in 2002 in Andijk, The Netherlands and has been asexually reproduced repeatedly by vegetative cuttings and tissue culture in Gilroy, Calif., and Andijk, The Netherlands over a two-year period. The plant has also been trialed at Gilroy, Calif., Andijk, The Netherlands. The present invention has been found to retain its distinctive characteristics through successive asexual propagations.

SUMMARY OF THE INVENTION

The following are the most outstanding and distinguishing characteristics of this new cultivar when grown under normal horticultural practices in Gilroy, Calif. and Andijk, The Netherlands.

1. A compact and rounded growth habit;
2. Excellent branching;
3. Very early flowering;
4. Good heat tolerance; and
5. Large, white flowers.

DESCRIPTION OF PHOTOGRAPH

This new *Argyranthemum* plant is illustrated by the accompanying photograph which shows blooms, buds, and foliage of the plant in full color; the colors shown are as true as can be reasonably obtained by conventional photographic procedures. The photograph is of a 4½-month-old plant grown in an eight-inch pot in a poly-covered greenhouse with natural light in a late winter/spring trial setting.

The accompanying photograph shows blooms, buds, mature foliage, and plant habit; the inset shows mature inflorescences.

DESCRIPTION OF THE NEW CULTIVAR

The following detailed descriptions set forth the distinctive characteristics of 'Arg Whit'. The data which define these characteristics were collected from asexual reproductions carried out in Gilroy, Calif. The plant history was taken on eight-month-old plants grown in one-gallon pots in a poly-covered greenhouse. Color readings were taken in the greenhouse in the spring/summer season under natural light. Color references are primarily to The R.H.S. Colour Chart of The Royal Horticultural Society of London (R.H.S.) (2001 edition). Texture description details were observed under a dissecting microscope.

DESCRIPTION OF THE NEW PLANT

Classification:
*Botanical name.*—*Argyranthemum frutescens.*
Parentage:
*Female parent.*—'ARO-2-6-1' proprietary line (unpatented).
*Male parent.*—'ARO-2-15-1' proprietary line (unpatented).
Growth:
*Form.*—Upright and slightly spreading.
*Habit.*—Compact and mounded.
*Growth and branching habit.*—Good, vigorous and freely branching habit.
*Height (from top of soil).*—35–40 cm.
*Width (including flowers).*—60–70 cm.
*Time to produce a finished flowering plant.*—7–9 weeks for a 6-inch pot.

*Outdoor plant performance.*—Used as patio planters, mixed-container plantings, or in garden beds.

*Time to initiate and develop roots.*—21–28 days at 68° F.–74° F.

*Root description.*—Fibrous, freely branching, and white.

Leaves:

*Arrangement.*—Alternate.

*Shape.*—Pinnatifid and deeply divided.

*Apex.*—Acute.

*Base.*—Attenuate.

*Margin.*—Entire.

*Length* (*fully expanded*).—3.4–4.5 cm.

*Width* (*fully expanded*).—2.0 cm.

*Color.*—Upper surface: RHS 137A. Lower surface: RHS 137C.

*Venation.*—Type: Parallel. Color: Upper surface: RHS 138B. Lower surface: Venation does not show on lower surface.

*Texture.*—Glabrous.

*Petiole.*—Color: RHS 137A. Length: 0.3–0.4 cm. Width: 0.2 cm. Texture: Glabrous.

Stems:

*Length.*—25–30 cm.

*Diameter.*—0.2–0.3 cm at non-woody stage; 0.6–0.8 cm at the woody stage.

*Internode length.*—1.0 cm.

*Color.*—RHS 138B for non-woody stems and closest to RHS 199D for woody stems.

*Texture.*—Glabrous.

*Anthocyanin.*—Absent.

Bud:

*Shape.*—Broadly ovate.

*Diameter.*—0.5–0.7 cm.

*Length.*—0.4–0.7 cm.

*Color* (*at tight bud, when starting to show color*).—RHS 155B.

Inflorescence:

*Type.*—Terminal and axillary inflorescences held above foliage; capitulum inflorescence on long peduncles.

*Blooming habit.*—Plants flower continuously from the spring through the fall.

*Quantity of inflorescences per plant.*—140–160 buds and inflorescences at any time.

*Lastingness of individual blooms on the plant.*—10–14 days.

*Fragrance.*—None.

*Inflorescence diameter.*—3.5–4.5 cm.

*Disc diameter.*—1.2–1.5 cm.

*Disc floret.*—Quantity (per inflorescence): 150–160. Shape: Densely massed, tubular, 5-parted and flared at the apex. Color: RHS 14A. Length: 0.5 cm. Diameter (at apex): 0.15 cm. Apex: Acute. Base: Fused.

*Ray floret.*—Quantity: 19–23 arranged in one whorl. Length: 1.1–1.4 cm. Width: 0.4–0.55 cm. Color (immature and mature): Upper surface: RHS N155B, but whiter. Lower surface: RHS N155B, but whiter. Apex: Emarginate to praemorse. Base: Fused. Margin: Entire. Texture: Papillose.

*Penduncle.*—Color: RHS 138B. Length: 9.5–11 cm. Diameter: 0.2 cm. Texture: Glabrous.

*Involucre bracts.*—Quantity (per inflorescence): 15. Shape: Elliptical to ovate. Length: 0.3–0.4 cm. Width: 0.2 cm. Color: Upper surface: RHS N138B with margins translucent and papery. Lower surface: RHS N138B with margins translucent and papery. Apex: Acute. Base: Cuneate. Margin: Entire. Texture: Glabrous.

Reproductive organs:

*Androecium.*—Location: Present on disc florets only. Anther: Pollen color: RHS 13A. Pollen amount: Moderate.

*Gynoecium.*—Location: Present on ray and disc florets. Pistil length: 0.6 cm. Stigma: Color: RHS 14B. Style: Length: 0.3 cm. Diameter: Less than 0.1 cm. Color: RHS 157B.

Fruit and seed set: Has not been observed.

Disease and insect resistance: Has not been observed.

COMPARISON WITH PARENTAL AND COMMERCIAL CULTIVARS

'Arg Whit' differs from the female parent, 'ARO-2-6-1' proprietary line (unpatented), in that 'Arg Whit' flowers earlier, has better branching, and has a more compact plant habit than 'ARO-2-6-1'.

'Arg Whit' differs from the male parent, 'ARO-2-15-1' proprietary line (unpatented), in that 'Arg Whit' flowers earlier, has bigger flowers, and has a more compact plant habit than 'ARO-2-15-1'.

'Arg Whit' differs from the commercial cultivar 'Argyrantis' (U.S. Plant Pat. No. 14,413) in that 'Arg Whit' blooms longer and has more flowers though the summer than 'Argyrantis'. Additionally, 'Arg Whit' has larger and fuller flowers and a more compact plant habit than 'Argyrantis'.

I claim:

1. A new and distinct cultivar of *Argyranthemum* plant as shown and described herein.

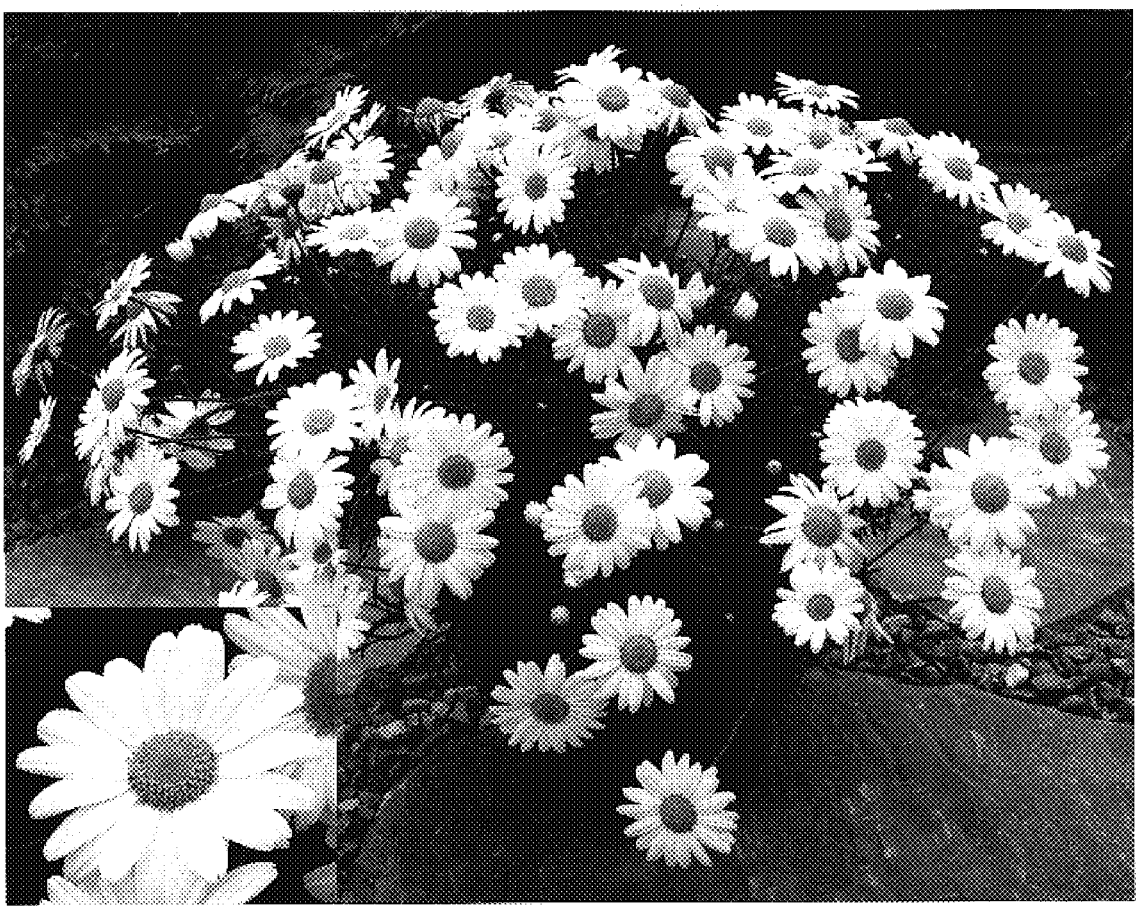

* * * * *